United States Patent [19]

Furman, Jr. et al.

[11] Patent Number: 5,234,913
[45] Date of Patent: Aug. 10, 1993

[54] ANTIVIRAL NUCLEOSIDE COMBINATION

[75] Inventors: Phillip A. Furman, Jr., Durham; George R. Painter, III, Chapel Hill, both of N.C.

[73] Assignee: Burroughs Wellcome Co., Research Triangle Park, N.C.

[21] Appl. No.: 846,367

[22] Filed: Mar. 5, 1992

[30] Foreign Application Priority Data

Mar. 6, 1991 [GB] United Kingdom ............... 9104740

[51] Int. Cl.⁵ .................... A61K 31/70; A61K 31/505
[52] U.S. Cl. ...................................... 514/49; 514/50; 514/274; 514/371; 536/28.2; 544/327
[58] Field of Search ...................... 514/42, 43; 536/23

[56] References Cited

U.S. PATENT DOCUMENTS

| 4,724,232 | 2/1988 | Rideout et al. | 514/50 |
| 4,837,311 | 6/1989 | Tam et al. | 536/22 |
| 4,874,751 | 10/1989 | Beacham et al. | 514/50 |
| 5,041,449 | 8/1991 | Belleau et al. | 514/274 |
| 5,047,407 | 9/1991 | Belleau et al. | 514/274 |
| 5,071,983 | 12/1991 | Koszalka et al. | 544/317 |

FOREIGN PATENT DOCUMENTS

| 0196185 | 10/1986 | European Pat. Off. . |
| 0206497 | 12/1986 | European Pat. Off. . |
| 0270317 | 6/1988 | European Pat. Off. . |
| 0337713 | 10/1989 | European Pat. Off. . |
| 0382526 | 8/1990 | European Pat. Off. . |
| 0494119 | 7/1992 | European Pat. Off. . |
| WO90/14079 | 11/1990 | PCT Int'l Appl. . |
| WO91/00867 | 1/1991 | PCT Int'l Appl. . |
| WO91/11186 | 8/1991 | PCT Int'l Appl. . |
| GB92/00389 | 5/1992 | PCT Int'l Appl. . |
| 92/08717 | 5/1992 | PCT Int'l Appl. . |

OTHER PUBLICATIONS

Belleau et al., "Design and Activity of a Novel Class of Nucleoside Analogs Effective Against HIV-1," 5th International AIDS Cong., Jun., 1989, p. 515, Abstr. No. T.C.O.1.

Rooke et al., "Biological Comparison of Wild-Type and Zidovudine-Resistant Isolates of Human Immunodeficiency Virus Type 1 from the Same Subjects: Susceptibility and Resistance to Other Drugs," Antimicrob. Agents Chemother., 35(5), 988-991 (1991).

Beach, et al., "Synthesis of (−)-L-Beta-BCH-189 from L-Glucose and its Anti-HIV and anti-HBV Activity," Abstracts of Papers from the 203rd ACS National Meeting, vol. 203(1-3), #50 (1992).

Greenberg, et al., "Metabolism, Toxicity and Anti-HIV Activity of 2'-Deoxy-3'-Thia-Cytidine (BCH-189) in T and B Cell Lines," Annals of the New York Academy of Sciences, vol. 616, pp. 517-518 (1990).

Beach, et al., "Synthesis of Enantiomerically Pure (2'R,5'S)-(−)1-{2-(Hydroxymethyl)oxathiolan-5-yl} cytosine as a Potent Antiviral Agent Against Hepatitis B Virus (HBV) and Human Immunodeficiency Virus (HIV)," J. Org. Chem. 57, 2217-2219 (1992).

Robbins, M. J., et al., Nucleic Acid Chemistry, Part 2, J. Wiley and Sons, New York, 895-900 (1978).

Duschinsky, R., Nucleic Acid Chemistry, Part 1, J. Wiley and Sons, New York, 43-46 (1978).

Schleicher and Schuell, S&S, 10 Optical Ave., Keene, N.H. 03431, Publication No. 700, 1987.

Southern, E. M., J. Mol. Biol, 98, 504-17 (1975).

Norbeck et al., Tetrahedron Letters, vol. 30, No. 46, pp. 6263-6266 (1989).

Abstract No. 90-248406/33, Eastman Kodak Co., EP-382-519-A.

Abstract No. 89-302435/42, IAF Biochem. Int., Inc., EP337-713-A.

(List continued on next page.)

Primary Examiner—Johnnie R. Brown
Assistant Examiner—L. Eric Crane
Attorney, Agent, or Firm—Donald Brown; Lawrence A. Nielsen; Hannah O. Green

[57] ABSTRACT

Synergistic combinations of nucleoside derivatives, pharmaceutical formulations containing said combinations and use of the combinations in the treatment of retroviral infections are disclosed.

5 Claims, No Drawings

OTHER PUBLICATIONS

Abstract No. 83654 c/47, Tanabe Seiyaku KK, J5 5130-975.

Abstract No. 99-314460/42, R. T. Walker, EP-392-791-A.

Abstract, Patent and Literature Search, IAF Biochem. Int., Inc.

Averett, D. R., J. Virol. Methods, 23, 263-276 (1989).

Elion, G. et al., J. Biol. Chem., 208, 477-88 (1954).

Kassianides, et al., "Effects of 2',3'-dideoxycytidine on Duck Hepatitis B Virus,"0 Gastroenterology 94 (5), part 2, p. A552 (1988).

Doong, et al., "Inhibition of the Replication of Hepatitis B Virus in vitro by 2',3'-dideoxy-3'thiacytidine and Related Analogues," Abstracts of the ICAAC, Abstract No. 496, p. 181 (Aug. 1991).

Soudeyns, H. et al., Antimicrob. Agents Chemother., 35 (7), 1386-90 (1991).

Choi, W. B. et al., J. Am. Chem. Soc., 113 (24), 9377-9 (1991).

Tyle, P., Pharmaceutical Research 3 (6), 318-26 (1986).

Halongquist, E. G. and Hibbert, H., Can. J. Research, 8, 129 1933.

Hesse, G. and Jorder, I., Chem. Ber. 85, 924, 932 (1952).

Busso et al., "Nucleotide Dimers Suppress HIV Expression In Vitro," *AIDS Research and Human Retroviruses*, 4(6), 449-455 (1988).

Doong et al., "Inhibition of the replication of hepatitis B virus in vitro by 2',3'-dideoxy-3'-thiacytidine and related analogs," *Proc. Nat. Acad. Sci. USA*, 88(19), 8494-8499 (1991); *Chem. Abstr.*, 115, p. 27, Abstr. No. 269987z (1991); only abstract provided.

K. J. Divakar, et al., J. Chem. Soc., Perkins 1, 1982, pp. 1171-1176, 4-(1,2,4-Triazol-1-yl)-and 4-(3-Nitro-1,2,4-triazol-1-yl)-1-($\beta$-D-2,3,5-tri--O-acetylarabinofurarosyl)pyrimidin-2(1H)-ones.

Valuable Intermediate in the Systhesis of Derivatives of 1-($\beta$-D-Arabinofuranosyl)cytosine (Ara-C).

Wing L. Sung, Nucleic Acids Research, vol. 9, No. 22, 1981, Synthesis of 4-triazolopyrimidinone nucleotide and its application in synthesis of 5-methylcytosine containing oligodeoxyribonucleotides, pp. 6139-6151.

Sells, et al., Proc. Natl. Acad. Sci., USA, vol. 84, Feb., 1987, pp. 1005-1009, Cell Biology, Production of hepatitis B virus particles in Hep G2 cells transfected with cloned hepatitis B virus DNA.

Sells, et al., Journal of Virology, vol. 62, No. 8, Aug., 1988, Replicative Intermediates of Hepatitis B Virus in HepG2 Cells That Produce Infectious Virions, pp. 2836-2844.

Abstract, Patent and literature search for 2'-deoxy-3'--thianucleoside analogues, as disclosed in EP 382526 (IAF Biochemical Int., Inc.).

Virology (Part 1), 5th International AIDS Congress, Jun. 1989.

ANTIVIRAL NUCLEOSIDE COMBINATION

The present invention relates to synergistic antiviral combinations of nucleoside derivatives, pharmaceutical formulations containing said combinations and their use in medical therapy, particularly in the treatment of virus infections, especially retrovirus infections.

Acquired immunodeficiency syndrome, (AIDS) is an immunosuppressive or immunodestructive disease that predisposes subjects to fatal opportunistic infections. Characteristically, AIDS is associated with a progressive depletion of T-cells, especially the helper-induced subset bearing the OKT$^4$ surface marker.

Human immunodeficiency virus (HIV) has been reproducibly isolated from patients with AIDS or with the symptoms that frequently precede AIDS. HIV is cytopathic and appears to preferentially infect and destroy T-cells bearing the OKT$^4$ marker. It is now generally recognized that HIV is the etiological agent of AIDS.

Since the discovery that HIV is the etiological agent of AIDS, numerous proposals have been made for anti-HIV chemotherapeutic agents that may be effective in treating AIDS sufferers. Thus, for example, European Patent Specification 0 382 526 describes anti-HIV substituted 1,3-oxathiolanes. U.S. Pat. No. 4,724,232 and European Specification 0 196 185 describe 3'-azido-3'-deoxythymidine (which has the approved name zidovudine) and its use in treating AIDS.

Since the priority date of this patent application, the following items have been published: Liotta, D. C. and Choi, W. B., Synthesis of BCH-189 and related compounds, PCT Appl. WO 91/11186; Soudeyns, H. et al., Anti-human immunodeficiency virus type 1 activity and in vitro toxicity of 2'-deoxy-3'-thiacytidine (BCH-189), Antimicrob. Agents Chemother., 35 (7), 1386–90 (1991); Choi, W. B. et al., In situ complexation directs the stereochemistry of N-glycosylation in the synthesis of thialanyl and dioxolanyl nucleoside analogs, J. Am. Chem. Soc., 113(24), 9377–9 (1991).

We have now discovered that 1-(2-hydroxymethyl)-1,3-oxathiolan-5-yl)-5-fluorocytosine in combination with 3'-azido-3'-deoxythymidine (zidovudine) results in a surprisingly large potentiation of the anti-HIV activity of the compounds. The use of 1-(2-(hydroxymethyl)-1,3-oxathiolan-5-yl)-5-fluorocytosine in conjunction with zidovudine produces a synergistic increase in anti-HIV activity in comparison with the anti-HIV activities of the individual compounds.

According to a first feature of the present invention there is provided a combination of (a) 1-(2-(hydroxymethyl)-1,3-oxathiolan-5-yl)-5-fluorocytosine of formula (I):

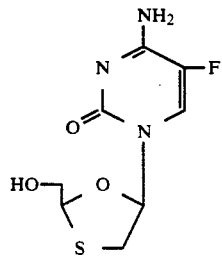

or a physiologically functional derivative thereof and (b) 3'-azido-3'-deoxythymidine (zidovudine) of formula (II):

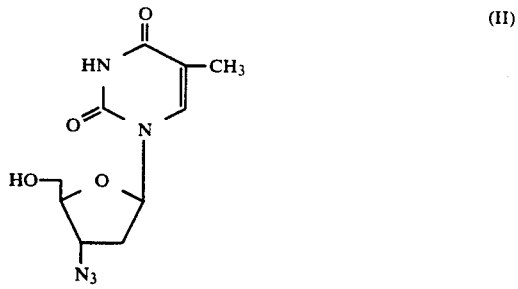

or a physiologically functional derivative thereof, components (a) and (b) of the combination being employed together such that a synergistic antiviral effect is achieved. The term "synergistic antiviral effect" is used herein to denote an antiviral effect which is greater than the predicted purely additive effects of the individual components (a) and (b) of the combination.

It should be noted that the compound of formula (I) contains two chiral centers and therefore exists in the form of two pairs of optical isomers (i.e. enantiomers) and mixtures thereof including racemic mixtures. Thus, the compound of formula (I) may be either a cis or a trans isomer or mixtures thereof. Each cis or a trans isomer or mixtures thereof. Each cis and trans isomer can exist as one of two enantiomers or mixtures thereof including racemic mixtures.

All such isomers and mixtures thereof including racemic mixtures are within the scope of the invention which also includes the tautomeric forms of the compounds of formula (I) and (II). The cis isomers of the compound of formula (I) are preferred.

By "physiologically functional derivative" is meant a pharmaceutically acceptable salt, ester or salt of an ester of the parent compound of formula (I) or (II), a pharmaceutically acceptable amide of the compound of (I), or any other compound which upon administration to the recipient is capable of providing (directly or indirectly) the parent compound or an active metabolite or residue thereof.

Preferred esters according to the invention include carboxylic acid esters in which the non-carbonyl moiety of the ester grouping is selected from straight or branched chain alkyl e.g. n-propyl, t-butyl, n-butyl, alkoxyalkyl (e.g. methoxymethyl), aralkyl (e.g. benzyl), aryloxyalkyl (e.g. phenoxymethyl), and aryl (e.g. phenyl); sulfonate esters such as alkyl- or aralkylsulfonyl (e.g. methanesulfonyl); amino acid esters (e.g. L-valyl or L-isoleucyl); dicarboxylic acid esters (e.g., hemisuccinate); and mono-, di- or triphosphate esters. The phosphate esters may be further esterified by, for example, a $C_{1-20}$ alcohol or reactive derivative thereof, or by a 2,3-di($C_{6-24}$)acyl glycerol.

Any alkyl moiety present in such esters advantageously contains 1 to 18 carbon atoms, particularly 1 to 4 carbon atoms. Any aryl moiety present in such esters advantageously comprises a phenyl group optionally substituted, e.g. by halogen, $C_{1-4}$ alkyl, $C_{1-4}$ alkoxy or nitro.

The above-mentioned pharmaceutically acceptable amides of the compound of formula (I) include those derivatives wherein the cytosine amino group is present in the form of an amide, e.g. NHCOR wherein R is $C_{1-6}$ alkyl or aryl (e.g. phenyl optionally substituted by halogen, $C_{1-4}$ alkyl, $C_{1-4}$ alkoxy, nitro or hydroxyl).

Examples of pharmaceutically acceptable salts include base salts, e.g. derived from an appropriate base, such as alkali metal (e.g. sodium), alkaline earth metal (e.g. magnesium) salts, ammonium and $NX_4^+$ (wherein X is $C_{1-4}$ alkyl). Pharmaceutically acceptable acid addition salts include salts of organic carboxylic acids such as acetic, lactic, tartaric, malic, isethionic, lactobionic and succinic acids; organic sulfonic acids such as methanesulfonic, ethanesulfonic, benzenesulfonic and p-toluenesulfonic acids and inorganic acids such as hydrochloric, sulfuric, phosphoric and sulfamic acids.

Examples of viral infections and associated clinical conditions which may be treated or prevented in accordance with the invention, include human retroviral infections such as human immunodeficiency virus (HIV), e.g. HIV-1 or HIV-2, and human T-cell lymphotropic virus (HTLV), e.g. HTLV-I or HTLV-II infections. The combinations of the present invention are especially useful for the treatment of AIDS and related clinical conditions such as AIDS-related complex (ARC), progressive generalized lymphadenopathy (PGL), AIDS-related neurological conditions, such as multiple sclerosis or tropical paraparesis, anti-HIV antibody-positive and HIV-positive conditions such as thrombocytopenic purpura. The combinations of the present invention may also be used in the treatment of psoriasis. The combinations of the present invention have been found to be particularly applicable to the treatment of asymptomatic infections or diseases caused by or associated with human retroviruses.

According to a second feature of the invention there are provided combinations as hereinbefore described, for use in medical therapy, particularly for the treatment or prophylaxis of any of the aforementioned viral infections or conditions, especially HIV infections including AIDS.

The present invention further includes a process for preparing the combinations hereinbefore described, which comprises bringing into association components (a) and (b) of the combination in a medicament to provide a synergistic antiviral effect. In a further aspect of the present invention, there is provided the use of a combination of the present invention in the manufacture of a medicament for the treatment of any of the aforementioned viral infections or conditions.

The present invention further provides a method for the treatment or prophylaxis of viral infections (especially HIV infections) in a mammal (including a human) which comprises administering to said mammal an effective amount of a combination as hereinbefore described. It will be appreciated that in accordance with the present invention, components (a) and (b) of the combination may be administered simultaneously or sequentially. In the latter case, however, the components are administered within a sufficiently short interval to ensure that a synergistic antiviral effect is achieved.

The present invention also provides a method of potentiating in a mammal (including a human) having a viral infection, the antiviral activities of components (a) and (b) of the combination, which comprises administering to said mammal an effective synergistic amount of component (a) simultaneously with, previous to, or subsequent to the administration of component (b).

An advantage of the combination of the present invention is that it enables attainment of an improved antiviral efficacy at a particular dose of one of the antiviral components (compared with the component used alone) thereby improving the therapeutic index of the component. Thus, for example, the combination may be used to treat conditions which would otherwise require relatively large doses of the antiviral component at which toxicity problems may occur. The smaller doses of the combination may provide increased convenience to the recipient and increased compliance.

The combinations of the present invention may be administered to a mammal in a conventional manner. As indicated above, components (a) and (b) may be administered simultaneously (e.g., in a unitary pharmaceutical formulation) or separately (e.g., in separate pharmaceutical formulations). In general, the combinations may be administered by the topical, oral, rectal or parenteral (e.g., intravenous, subcutaneous or intramuscular) routes. It will be appreciated that the route may vary with, for example, the severity of the condition to the treated and the identity of the recipient.

It will be appreciated that, while there will usually be an optimum ratio of the components to ensure maximum potentiation, even a vanishingly small quantity of one component will suffice to potentiate the effect of the other to some degree, and so any ratio of two potentiating components will still possess the required synergistic effect. However, greatest synergy is generally observed when the two components are present in particular ratios.

Thus the optimum molar ratios of zidovudine to 1-(2-(hydroxymethyl)-1,3-oxathiolan-5-yl)-5-fluorocytosine, or their respective physiologically functional derivatives, for use according to this invention are from 1:1 to 1:600, preferably from 1:10 to 1:250, and most preferably 1:25.

Hereafter the components of the combination may be referred to as "active ingredients".

The dose of the combination will depend on the condition being treated and other clinical factors such as the weight and condition of the recipient and the route of administration of the components of the combinations. Examples of dose ranges and component ratios are as follows:

In general a suitable dose of a combination of the present invention based on the total weight of components (a) and (b) will be in the range of 3 to 120 mg per kilogram body weight of the recipient per day, preferably in the range of 6 to 90 mg per kilogram body weight per day and most preferably in the range 15 to 60 mg per kilogram body weight per day. The desired dose is preferably presented as two, three, four, five, six or more sub-doses administered at appropriate intervals throughout the day. These sub-doses may be administered in unit dose forms, for example, containing 10 to 1500 mg, preferably 20 to 1000 mg, and most preferably 50 to 700 mg of active ingredients per unit dose form.

While it is possible for the active ingredients to be administered alone it is preferable to present them as pharmaceutical formulations. Pharmaceutical formulations of the present invention comprise a combination according to the invention together with one or more pharmaceutically acceptable carriers or excipients and optionally other therapeutic agents. When the individual components of the combination are administered separately they are generally each presented as a pharmaceutical formulation. The references hereinafter to formulations refer unless otherwise stated to formulations containing either the combination or a component thereof. Formulations include those suitable for oral, rectal, nasal, topical (including transdermal, buccal and sublingual), vaginal or parenteral (including subcutaneous, intramuscular, intravenous and intradermal) administration. The formulations may conveniently be presented in unit dosage form and may be prepared by any methods well known in the art of pharmacy. Such methods include the step of bringing into association the active ingredients with the carrier which constitutes one or more accessory ingredients.

In general, the formulations are prepared by uniformly and intimately bringing into association the active ingredients with liquid carriers or finely divided solid carriers or both, and then if necessary shaping the product.

Formulations of the present invention suitable for oral administration may be presented as discrete units such as capsules, cachets or tablets each containing a predetermined amount of the active ingredients; as a powder or granules; as a solution or a suspension in an aqueous or non-aqueous liquid; or as an oil-in-water liquid emulsion or a water-in-oil liquid emulsion. The active ingredient may also be presented as a bolus, electuary or paste.

A tablet may be made by compression or molding, optionally with one or more accessory ingredients. Compressed tablets may be prepared by compressing in a suitable machine the active ingredients in a free-flowing form such as a powder or granules, optionally mixed with a binder (e.g. povidone, gelatin, hydroxypropylmethyl cellulose), lubricant, inert diluent, preservative, disintegrant (e.g. sodium starch glycollate, cross-linked povidone, cross-linked sodium carboxymethyl cellulose) surface-active or dispersing agent. Molded tablets may be made by molding a mixture of the powdered compound moistened with an inert liquid diluent in a suitable machine. The tablets may optionally be coated or scored and may be formulated so as to provide slow or controlled release of the active ingredients therein using, for example, hydroxypropylmethyl cellulose in varying proportions to provide the desired release profile. Tablets may optionally be provided with an enteric coating, to provide release in parts of the gut other than the stomach.

Formulations suitable for topical administration in the mouth include lozenges comprising the active ingredients in a flavored base, usually sucrose and acacia or tragacanth; pastilles comprising the active ingredient in an inert basis such as gelatin and glycerin, or sucrose and acacia; and mouthwashes comprising the active ingredient in a suitable liquid carrier. Formulations for rectal administration may be presented as a suppository with a suitable base comprising, for example, cocoa butter or a salicylate.

Topical administration may also be by means of a transdermal iontophoretic device. Formulations suitable for vaginal administration may be presented as pessaries, tampons, creams, gels, pastes, foams or spray formulations containing in addition to the active ingredient such carriers as are known in the art to be appropriate.

Formulations suitable for parenteral administration include aqueous and nonaqueous isotonic sterile injection solutions which may contain anti-oxidants, buffers, bacteriostats and solutes which render the formulation isotonic with the boood of the intended recipient; and aqueous and non-aqueous sterile suspensions which may include suspending agents and thickening agents; and liposomes or other microparticulate systems which are designed to target the compound to blood components or one or more organs. The formulations may be presented in unit-dose or multi-dose sealed containers, for example, ampules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets of the kind previously described.

Preferred unit dosage formulations are those containing a daily dose or daily subdose of the active ingredients, as hereinbefore recited, or an appropriate fraction thereof.

It should be understood that in addition to the ingredients particularly mentioned above the formulations of this invention may include other agents conventional in the art having regard to the type of formulation in question, for example, those suitable for oral administration may include such further agents as sweeteners, thickeners and flavoring agents.

The compounds of the combination of the present invention may be prepared in conventional manner. Zidovudine can be prepared, for example, as described in U.S. Pat. No. 4,724,232, incorporated herein by reference. Zidovudine can also be obtained from Aldrich Chemical Co., Milwaukee, WI 53233, USA.

1-(2-(Hydroxymethyl)-1,3-oxathiolan-5-yl)-5-fluorocytosine may be prepared for example by:

a) reacting optionally protected 5-fluorocytosine with a 1,3-oxathiolane of formula (IIIA):

wherein $R_1$ is hydrogen or a hydroxy protecting group and L is a leaving group; or b) reacting a compound of formula (IIIB):

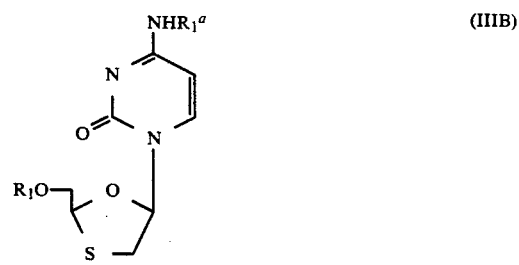

(wherein $R_1$ is as defined above and $R_1^a$ is an amino protecting group) with a fluorinating agent serving to introduce a fluorine atom in the 5-position of the cytosine ring; or c) reacting a compound of formula (IIIC):

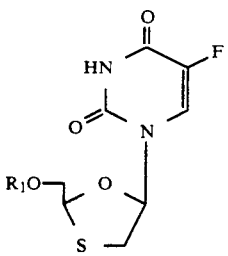

(IIIC)

(wherein $R_1$ is as defined above) with an agent serving to convert the oxo group in the 4-position of the uracil ring to an amino group; any remaining protecting groups being removed to produce the desired product.

With the regard to process a), the hydroxy protecting group includes protecting groups such as acyl (e.g. acetyl), arylacyl (e.g. benzoyl or substituted benzoyl, trialkylsilyl (e.g. dimethyl-t-butylsilyl) or diphenylmethylsilyl. The 5-fluorocytosine compound may be optionally protected with silyl, e.g. trimethyl silyl groups. Such groups may be removed in conventional manner. The leaving group L is a leaving group typical of those known in the art of nucleoside chemistry e.g. halogen such as chlorine or bromine, alkoxy such as methoxy or ethoxy or acyl such as acetyl or benzoyl.

The reaction in process a) may be affected in an organic solvent (e.g. 1,2-dichloroethane or acetonitrile) in the presence of a Lewis acid such as stannic chloride or trimethylsilyl triflate.

Compounds of formula (IIIA) may be obtained from a suitably protected 2-hydroxyacetaldehyde of formula (IV):

$$R_1OCH_2CHO \qquad (IV)$$

wherein $R_1$ is defined above, as described in *Can. J. Research*, 8, 129 (1933) and European Patent Specification 0 382 526. Reaction of compounds of formula IV with a mercaptoacetal $HSCH_2CH(OR)_2$ wherein R is $C_{1-4}$ alkoxy such as $HSCH_2CH(OC_2H_5)_2$, known in the art (*Chem. Ber.* 85, 924–932 (1952)), yields compounds of formula (IIIA) wherein L is OR (alkoxy) e.g. methoxy or ethoxy. Alternatively, compounds of formula IIIA, wherein L is alkoxy, may be converted to compounds of formula IIIA wherein L is halogen or acyl by methods known in the art of carbohydrate chemistry.

Compounds of formula (IV) may be prepared from 1,2-O-isopropylidene glycerol by introduction of $R_1$ (e.g. trisubstituted silyl, benzyl or trityl) and removal of the isopropylidene group with mild acid (e.g. aqueous formic or acetic acid) or zinc bromide in acetonitrile, followed by oxidation of the alcohol group with aqueous periodate.

With regard to process b), the 5-fluoro substituent may be introduced by methods known in the art (M. J. Robins, et al., in Nucleic Acid Chemistry. Part 2, L. B. Townsend and R. S. Tipson, editors, J. Wiley and Sons, New York, 895–900 (1978) and reference therein; R. Duschinsky in Nucleic Acid Chemistry, Part 1, L. B. Townsend and R. S. Tipson, editors, J. Wiley and Sons, New York, 43–46 (1978) and references therein). The fluorinating agent may be, for example, trimethylhypofluorite in fluorotrichloromethane.

With regard to process c), the compound of formula (IIIC) is advantageously treated with 1,2,4-triazole, advantageously together with 4-chlorophenyl dichlorophosphate, to form the corresponding 4-(1,2,4-triazoyl) compound which is then converted to the desired 4-amino (cytidine) compound by reaction with for example methanol.

The starting materials of formulas (IIIB) and (IIIC) may be prepared for example by reaction of an appropriate (optionally protected) base with a compound of formula (IIIA) in an analogous manner to that described in process a). 5-Fluorouracil and 5-fluorocytosine are commercially available from Aldrich Chemical Co., Milwaukee, WI 53233, USA.

Separation of the (±)-cis and (±)-trans isomers of formula (I) for example in a protected form, may be accomplished by chromatography on silica gel with mixtures of organic solvents such as ethyl acetate/methanol, ethyl acetate/hexane or dichloromethane/methanol. Any protecting group may then be removed using the appropriate reagent for each group.

Esters of the component compounds of formulas (I) and (II) may be prepared in conventional manner by reaction with an appropriate esterifying agent such as an acid halide or anhydride. The compounds of formulas I and II or esters thereof may be converted into pharmaceutically acceptable salts thereof by treatment with an appropriate base. An ester or salt of the component compounds may be converted into the parent compound by hydrolysis.

Pharmaceutically acceptable amides of the compound of formula (I) may be prepared, for example by reaction with an appropriate acylating agent, for example, an acid halide or anhydride serving to acylate the 5'-OH and 4-$NH_2$ groups. The acyl group may then be removed selectively from one or other of the 5'-OH and 4-$NH_2$ groups. For example, treatment of the diacylated compound under acidic conditions, e.g. a Lewis acid such as zinc bromide in methanol, removes the 4N-acyl group to yield the corresponding 5'-OH ester, while treatment of the diacylated compound under alkaline conditions, e.g. with sodium methoxide removes the 5'-OH acyl group to yield the corresponding 4N-amide. The acyl groups can also be removed selectively by treatment with commercially available esterase or lipase enzymes, e.g. pig liver esterase or pancreatic lipase, or by treatment in accordance with methods described in U.S. Pat. No. 5,071,983. The compound of formula (I) may be converted into a pharmaceutically acceptable salt thereof in a conventional manner, for example, by treatment with an appropriate base.

The following examples are intended for illustration only and are not intended to limit the scope of the invention in any way. "Active ingredient" denotes a mixture of the components zidovudine and cis-1-(2-(hydroxymethyl)-1,3-oxathiolan-5-yl)-5-fluorocytosine in the molar ratio of 1:25.

EXAMPLE 1

Tablet Formulation

The following formulations A, B and C are prepared by wet granulation of the ingredients with a solution of povidone, followed by addition of magnesium stearate and compression.

Formulation A

|  | mg/tablet |
| --- | --- |
| Active Ingredient | 250 |

-continued

|  | mg/tablet |
|---|---|
| Lactose B.P. | 210 |
| Povidone B.P. | 15 |
| Sodium Starch Glycollate | 20 |
| Magnesium Stearate | 5 |
|  | 500 |

Formulation B

|  | mg/tablet |
|---|---|
| Active Ingredient | 250 |
| Lactose B.P. | 150 |
| Avicel PH 101 | 60 |
| Povidone B.P. | 15 |
| Sodium Starch Glycollate | 20 |
| Magnesium Stearate | 5 |
|  | 500 |

Formulation C

|  | mg/tablet |
|---|---|
| Active Ingredient | 250 |
| Lactose B.P. | 200 |
| Starch | 50 |
| Povidone | 5 |
| Magnesium Stearate | 4 |
|  | 359 |

The following formulations, D and E, are prepared by direct compression of the admixed ingredients. The lactose in formulation E is of the direct compression type (Dairy Crest—"Zeparox").

Formulation D

|  | mg/tablet |
|---|---|
| Active Ingredient | 250 |
| Pregelatinized Starch NF15 | 150 |
|  | 400 |

Formulation E

|  | mg/tablet |
|---|---|
| Active Ingredient | 250 |
| Lactose B.P. | 150 |
| Avicel | 100 |
|  | 500 |

Formulation F (Controlled Release Formulation)

The formulation is prepared by wet granulation of the ingredients with a solution of povidone followed by the addition of magnesium stearate and compression.

|  | mg/tablet |
|---|---|
| Active Ingredient | 500 |
| Hydroxypropylmethylcellulose (Methocel K4M Premium) | 112 |
| Lactose B.P. | 53 |
| Povidone B.P. | 28 |
| Magnesium Stearate | 7 |

-continued

|  | mg/tablet |
|---|---|
|  | 700 |

Drug release takes place over a period of about 6–8 hours and is complete after 12 hours.

EXAMPLE 2

Capsule Formulations

Formulation A

A capsule formulation is prepared by admixing the ingredients of formulation D in Example 1 above and filling into a two-part hard gelatin capsule. Formulation B (infra) is prepared in a similar manner.

Formulation B

|  | mg/capsule |
|---|---|
| Active Ingredient | 250 |
| Lactose B.P. | 143 |
| Sodium Starch Glycollate | 25 |
| Magnesium Stearate | 2 |
|  | 420 |

Formulation C

|  | mg/capsule |
|---|---|
| Active Ingredient | 250 |
| Macrogel 4000 B.P. | 350 |
|  | 600 |

Capsules of formulation C are prepared by melting the Macrogel 4000 B.P., dispersing the active ingredient in the melt and filling the melt into a two-part hard gelatin capsule.

Formulation D

|  | mg/capsule |
|---|---|
| Active Ingredient | 250 |
| Lecithin | 100 |
| Arachis Oil | 100 |
|  | 450 |

Capsules of formulation D are prepared by dispersing the active ingredient in the lecithin and arachis oil and filling the dispersion into soft, elastic gelatin capsules.

Formulation E (Controlled Release Capsule)

The following controlled release capsule formulation is prepared by extruding ingredients a, b, and c using an extruder, followed by spheronization of the extrudate and drying. The dried pellets are then coated with release-controlling membrane (d) and filled into a two-piece, hard gelatin capsule.

|  | mg/capsule |
|---|---|
| (a) Active Ingredient | 250 |
| (b) Microcrystalline Cellulose | 125 |
| (c) Lactose B.P. | 125 |
| (d) Ethyl Cellulose | 13 |
|  | 513 |

EXAMPLE 3

Injectable Formulation

Formulation A

|  | mg |
|---|---|
| Active Ingredient | 200 |
| Hydrochloric Acid Solution 0.1M or | 4.0 to 7.0 |
| Sodium Hydroxide Solution 0.1M q.s. to pH | |
| Sterile water q.s. to | 10 ml |

The active ingredient is dissolved in most of the water (35°–40° C.) and the pH adjusted to between 4.0 and 7.0 with the hydrochloric acid or the sodium hydroxide as appropriate. The batch is then made up to volume with the water and filtered through a sterile micropore filter into a sterile 10 ml amber glass vial (type 1) and sealed with sterile closures and overseals.

Formulation B

| Active Ingredient | 125 mg |
|---|---|
| Sterile, Pyrogen-free, pH 7 Phosphate Buffer, q. s. to | 25 ml |

EXAMPLE 4

Intramuscular injection

| Active Ingredient | 200 mg |
|---|---|
| Benzyl Alcohol | 0.10 g |
| Glycofurol 75 | 1.45 g |
| Water for injection q.s. to | 3.00 ml |

The active ingredient is dissolved in the glycofurol. The benzyl alcohol is then added and dissolved, and water added to 3 ml. The mixture is then filtered through a sterile micropore filter and sealed in sterile 3 ml amber glass vials (type 1).

EXAMPLE 5

Syrup

| Active Ingredient | 250 mg |
|---|---|
| Sorbitol Solution | 1.50 g |
| Glycerol | 2.00 g |
| Sodium Benzoate | 0.005 g |
| Flavor, Peach 17.42.3169 | 0.0125 ml |
| Purified Water q.s. to | 5.00 ml |

The active ingredient is dissolved in a mixture of the glycerol and most of the purified water. An aqueous solution of the sodium benzoate is then added to the solution, followed by addition of the sorbital solution and finally the flavor. The volume is made up with purified water and mixed well.

EXAMPLE 6

Suppository

|  | mg/capsule suppository |
|---|---|
| Active Ingredient | 250 |
| Hard Fat, B.P. (Witepsol H15 - Dynamit Nobel) | 1770 |

-continued

|  | mg/capsule suppository |
|---|---|
|  | 2020 |

One-fifth of the Witepsol H15 is melted in a steam-jacketed pan at 45° C. maximum. The active ingredient is sifted through a 200 μm sieve and added to the molten base with mixing, using a Silverson fitted with a cutting head, until a smooth dispersion is achieved. Maintaining the mixture at 45° C., the remaining Witepsol H15 is added to the suspension and stirred to ensure a homogenous mix. The entire suspension is passed through a 250 μm stainless steel screen and, with continuous stirring, is allowed to cool to 40° C. At a temperature of 38° C. to 40° C., 2.02 g of the mixture is filled into suitable, 2 ml plastic molds. The suppositories are allowed to cool to room temperature.

EXAMPLE 7

Pessaries

|  | mg/pessary |
|---|---|
| Active Ingredient | 250 |
| Anhydrate Dextrose | 380 |
| Potato Starch | 363 |
| Magnesium Stearate | 7 |
|  | 1000 |

The above ingredients are mixed directly and pessaries prepared by direct compression of the resulting mixture.

EXAMPLE 8

Preparation of 1-(2-(hydroxymethyl)-1,3-oxathiolan-5-yl)-5-fluorocytosine

Method A ($\pm$)-cis and ($\pm$)-trans 2-benzoyloxymethyl-5-($N_4$-acetylcytosin-1-yl)-1,3-oxathiolane are prepared and separated to the ($\pm$)-cis and ($\pm$)-trans isomers as described in European Patent (EP) Specification 0 382 526. (See U.S. Pat. No. 5,047,407.) The ($\pm$)-cis isomer is fluorinated with trifluoromethyl hypofluorite in fluorotrichloromethane ($CCl_3F$) and chloroform at $-78°$ C., according to the method of Robins, et al. Nucleic Acid Chemistry, Part 2, 895–900 (1978). The $N_4$-acetyl and 2-benzoyl groups are removed with dimethylamine in ethanol, and the product, ($\pm$)-cis-1-(2-(hydroxymethyl)-1,3 -oxathiolan-5-yl)-5-fluorocytosine, is isolated.

Method B ($\pm$)-cis and ($\pm$)-trans 2-benzoyloxymethyl-5-(uracil-1-yl)-1,3-oxathiolane are prepared as described in EP 0 382 526). After deprotection of the 2-hydroxyl group with saturated methanolic ammonia, the isomers are separated on silica gel using EtOAc/MeOH as eluant (EP 0 382 526). The ($\pm$)-cis isomer is reacted with acetic anhydride in pyridine at room temperature to give the 2-acetate. Solvent is removed in vacuo at $<30°$ C. The 2-acetate is then dissolved in $CHCl_3$ and washed with aqueous bicarbonate. The separated organic layer is dried, and $CHCl_3$ is evaporated in vacuo. ($\pm$)-cis-2-Acetyl-oxymethyl-5-(uracil-1-yl)-1,3-oxathiolane is fluorinated as described above (Method A) by the method of Robins et al. Conversion of the 5-F-uracil base to the 5-F-cytosine base is carried out by preparation of the 4-(1,2,4-triazol-1-yl) derivative according to the methods of C. B. Reese, *J. Chem. Soc.*, Perkins I, 1171 (1984) and W. L. Sung, *Nucleic Acids Res.*, 9, 6139 (1981), using 1,2,4-triazole and 2 equivalents of 4-chlorophenyldichlorophosphate in dry pyridine at ambient temperature. This conversion is followed by reaction with methanol previously saturated with ammonia at 0° C, and the 2-acetate is hydrolyzed to give (±)-cis-1-(2-hydroxymethyl)-1,3-oxathiolan-5-yl)-5-fluorocytosine.

Antiviral Activity

Combinations according to the invention were tested for anti-HIV activity in an HIV-infected MT4 cell assay as described in Averett, D. R., *J. Virol. Methods*, 23, 263-276 (1989). The cells were exposed to HIV for one hour prior to addition of antiviral component(s). Components were tested in serial 2.5-fold dilutions. After five days of incubation at 37° C., the cell number was determined. Inhibition of HIV-induced cytopathic effect was calculated, and synergism was determined by FIC plots as described by Elion, Singer, and Hitchings, *J. Biol. Chem.* 208, 477 (1954).

The fractional inhibitor concentrations (FIC) of zidovudine and cis-1-(2-(hydroxymethyl)-1,3-oxathiolan-5-yl)-5-fluorocytosine were calculated according to the method of Elion et al., supra (Table 1).

These values can be plotted on a graph from which it can be determined that the combination of cis-1-(2-(hydroxymethyl)-1,3-oxathiolan-5-yl)-5-fluorocytosine and zidovudine is strongly synergistic.

TABLE 1

| | Calculation of Fractional Inhibitor Concentration (FIC) 70% Inhibition | | |
|---|---|---|---|
| Zidovudine (1M) | Compound 1* (1M) | FIC Zidovudine | FIA Compound 1 |
| 0.004 | 2.5 | 0.018 | 0.48 |
| 0.01 | 2.0 | 0.045 | 0.38 |
| 0.0256 | 1.6 | 0.12 | 0.31 |
| 0.06 | 1.4 | 0.27 | 0.26 |
| 0.22 | — | | |
| — | 5.2 | | |

*Compound 1 is cis-1-(2-(hydroxymethyl)-1,3-oxathiolan-5-yl)-5-fluorocytosine.

We claim:
1. A pharmaceutical composition comprising in admixture with a pharmaceutically acceptable carrier the components:
   (a) cis-1-(2-(hydroxymethyl)-1,3-oxathiolan-5-yl)-5-fluorocytosine or a pharmaceutically acceptable salt thereof and
   (b) 3'-azido-3'-deoxythymidine or a pharmaceutically acceptable salt thereof.
2. A pharmaceutical composition as claimed in claim 1, where component (a) is cis-1-(2-(hydroxymethyl)-1,3-oxathiolan-5-yl)-5-fluorocytosine and component (b) is 3'-azido-3'-deoxythymidine.
3. A pharmaceutical composition as claimed in claim 1 or claim 2, wherein the components are employed in a molar ration in the range from 600:1 to 1:1 of component (a) to component (b).
4. A pharmaceutical composition as claimed in claim 3, wherein the components are employed in a molar ration in the range from 250:1 to 10:1 of component (a) to component (b).
5. A pharmaceutical composition as claimed in claim 1, in the form of a tablet or capsule.